(12) United States Patent
Rassman et al.

(10) Patent No.: US 7,193,711 B2
(45) Date of Patent: *Mar. 20, 2007

(54) IMAGING METHOD AND APPARATUS

(75) Inventors: William Rassman, Los Angeles, CA (US); David Ralin, South Pasadena, CA (US); Robert A. Lieberman, Torrance, CA (US); Lothar U. Kempen, Redondo Beach, CA (US); Herbert Shapiro, Laguna Niguel, CA (US)

(73) Assignee: Maven Technologies, LLC, Los Angeles, CA (US)

( * ) Notice: Subject to any disclaimer, the term of this patent is extended or adjusted under 35 U.S.C. 154(b) by 273 days.

This patent is subject to a terminal disclaimer.

(21) Appl. No.: 10/847,736

(22) Filed: May 17, 2004

(65) Prior Publication Data

US 2005/0024642 A1    Feb. 3, 2005

Related U.S. Application Data

(63) Continuation-in-part of application No. 10/602,555, filed on Jun. 23, 2003, now Pat. No. 6,859,280, and a continuation-in-part of application No. 10/046,620, filed on Jan. 12, 2002, now Pat. No. 6,833,920, and a continuation-in-part of application No. 09/838,700, filed on Apr. 19, 2001, now Pat. No. 7,023,547, which is a continuation-in-part of application No. 09/614,503, filed on Jul. 11, 2000, now Pat. No. 6,594,011.

(51) Int. Cl.
*G01J 4/00* (2006.01)

(52) U.S. Cl. .................... 356/369; 356/445; 436/805

(58) Field of Classification Search ........ 356/317–318, 356/445, 244–246, 364–369, 128, 136, 446; 436/517, 805, 527; 422/82.08, 11, 82; 435/6, 435/7.1
See application file for complete search history.

(56) References Cited

U.S. PATENT DOCUMENTS 4,238,565 A    12/1980 Hornby et al.

(Continued)

FOREIGN PATENT DOCUMENTS

AU    742417    2/2000

(Continued)

OTHER PUBLICATIONS

Tadashi Saitoh, et al. "Optical Characterization of Very Thin Hydrogenated Amorphous Silicon Films Using Spectroscopic Ellipsometry"; Japanese Journal of Applied Physics; vol. 30, No. 11B, Nov. 1991. pp. L1914-L1916.

(Continued)

*Primary Examiner*—Layla G. Lauchman
*Assistant Examiner*—Tri Ton
(74) *Attorney, Agent, or Firm*—MacPherson Kwok Chen & Heid LLP; David S. Park

(57) ABSTRACT

An imaging method and apparatus are provided, including a light source emitting a polarized light beam, and an optical assembly including a control layer and/or a light reflection surface. The control layer advantageously allows for control over the properties of a generated evanescent wave to optimize an image of a specimen array within the evanescent wave. The light reflection surface includes coupling means used to couple a receptor/capture agent advantageously allowing for flexible control over receptor specific regions.

31 Claims, 2 Drawing Sheets

U.S. PATENT DOCUMENTS

| | | | |
|---|---|---|---|
| 4,256,834 A | 3/1981 | Zuk et al. | |
| 4,508,832 A | 4/1985 | Carter et al. | |
| 5,164,589 A | 11/1992 | Sjoedin | |
| 5,229,833 A | 7/1993 | Stewart | |
| 5,255,075 A | 10/1993 | Cush | |
| 5,313,264 A | 5/1994 | Ivarsson et al. | |
| 5,437,840 A | 8/1995 | King et al. | |
| 5,483,346 A | 1/1996 | Butzer | |
| 5,485,277 A | 1/1996 | Foster | |
| 5,491,097 A * | 2/1996 | Ribi et al. | 436/518 |
| 5,491,556 A | 2/1996 | Stewart et al. | |
| 5,573,956 A | 11/1996 | Hanning | |
| 5,593,130 A | 1/1997 | Hansson et al. | |
| 5,633,724 A | 5/1997 | King et al. | |
| 5,641,640 A | 6/1997 | Hanning | |
| RE35,716 E | 1/1998 | Stapleton et al. | |
| 5,753,518 A | 5/1998 | Karlsson | |
| 5,856,873 A | 1/1999 | Naya et al. | |
| 5,922,594 A | 7/1999 | Loefas | |
| 5,922,604 A | 7/1999 | Stapleton et al. | |
| 5,955,729 A | 9/1999 | Nelson et al. | |
| 5,965,456 A | 10/1999 | Malmqvist et al. | |
| 5,972,612 A | 10/1999 | Malmqvist et al. | |
| 6,008,010 A | 12/1999 | Greenberger et al. | |
| 6,008,893 A | 12/1999 | Roos et al. | |
| 6,045,996 A | 4/2000 | Cronin et al. | |
| 6,127,183 A | 10/2000 | Ivarsson et al. | |
| 6,140,044 A | 10/2000 | Bessemer et al. | |
| 6,143,513 A | 11/2000 | Loefas | |
| 6,143,574 A | 11/2000 | Karlsson et al. | |
| 6,197,595 B1 | 3/2001 | Anderson et al. | |
| 6,200,814 B1 | 3/2001 | Malmqvist et al. | |
| 6,207,381 B1 | 3/2001 | Larsson et al. | |
| 6,277,330 B1 | 8/2001 | Liu et al. | |
| 6,289,286 B1 | 9/2001 | Andersson et al. | |
| 6,355,429 B1 * | 3/2002 | Nygren et al. | 435/6 |
| 6,493,097 B1 | 12/2002 | Ivarsson | |
| 6,503,760 B2 | 1/2003 | Malmqvist et al. | |
| D472,644 S | 4/2003 | Dawson et al. | |
| 6,589,798 B1 | 7/2003 | Loefas | |
| 6,594,011 B1 | 7/2003 | Kempen | |
| D480,149 S | 9/2003 | Dawson et al. | |
| 6,698,454 B2 | 3/2004 | Sjoelander et al. | |
| 6,710,870 B1 * | 3/2004 | Marowsky et al. | 356/317 |
| 6,859,280 B2 * | 2/2005 | Kempen | 356/369 |
| 7,045,287 B2 * | 5/2006 | Smith et al. | 435/6 |
| 2002/0019019 A1 | 2/2002 | Hamalainen et al. | |
| 2002/0154311 A1 | 10/2002 | Ivarsson | |
| 2002/0182717 A1 | 12/2002 | Karlsson | |
| 2003/0022388 A1 | 1/2003 | Roos et al. | |
| 2003/0067612 A1 | 4/2003 | Ivarsson | |
| 2003/0112432 A1 * | 6/2003 | Yguerabide et al. | 356/317 |
| 2004/0002167 A1 | 1/2004 | Andersson et al. | |
| 2004/0012676 A1 | 1/2004 | Weiner et al. | |
| 2004/0023247 A1 | 2/2004 | Xu et al. | |
| 2004/0030504 A1 | 2/2004 | Helt et al. | |
| 2004/0038268 A1 | 2/2004 | Pirrung et al. | |

FOREIGN PATENT DOCUMENTS

| | | |
|---|---|---|
| WO | WO 96/08720 | 3/1996 |
| WO | WO 96/38729 | 12/1996 |
| WO | WO 97/19375 | 5/1997 |
| WO | WO 98/32002 | 7/1998 |
| WO | WO 03/056337 A1 | 7/2003 |
| WO | WO 03/102580 A1 | 12/2003 |

OTHER PUBLICATIONS

"Handbook of Optics", Michael Bass Editor in Chief, by The Optical Society of America; vol. 1; pp. 4.23, 4.24; 1995 McGraw-Hill, Inc.

Bass, et al. "Handbook of Optics", by The Optical Society of America; vol. 1; Section 41.10; 1995 McGraw-Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930-2936, Aug. 1996.

Max Born et al. "Principles of Optics—Electromagnetic Theory of Propagation, Interference and Diffraction of Light", Sixth Edition, pp. 47-51 Pergamon Press.

Eggins, "Biosensors: An Introduction", pp. 112-113, 1987 John Wiley & Sons.

Danny Van Noort et al. "Monitoring Specific Interaction of Low Molecular Weight Biomolecules on Oxidized Porous Silicon Using Ellipsometry", Biosensors & Bioelectronics vol. 13, No. 3-4 pp. 439-449, 1998 Elsevier Science, S.A. Great Britain.

Gang Jin et al. "Imaging Ellipsometry for Biosensor Applications" Transducers '95. Eurosensors IX, Digest of Technical Papers vol. 2, Sessions A7-D13, Papers No 232-496 pp. 509-512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44-50, 1992.

Ulf Jonsson et al. "Flow-Injection Ellipsometry—An in Situ Method for the Study of Biomolecular Adsorption and Interaction at Solid Surfaces," Colloids and Surfaces, 13 (1985) pp. 333-339, 1985 Elsevier Science Publishers BV, Amsterdam, The Netherlands.

Jonsson, Ulf et al. "Biosensors Based on Surface Concentration Measuring Devices—The Concept of Surface Concentration" Progress in Colloid and Polymer Sci. vol. 70, pp. 96-100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD, Mark, "Microarray Biochip Technology" TeleChem International, Inc., Sunnyvale, California, USA, A BioTechniques Books Publication, Eaton Publishing, pp. 10-11, 2000.

Harland G. Tompkins, et al. "Spectroscopic Ellipsometry and Reflectometry A User's Guide" A Wiley-Interscience Publication, John Wiley & Sons, Inc., 1999.

Ulf Jonsson et al. "Surface Immobilization Techniques in Combination with Ellipsometry" Methods in Enzymology vol. 137, Immobilized Enzymes and Cells Part D pp. 381-1351, 1988 Academic Press, Inc. Harcourt Brace Jovanovich, Publishers.

CH Striebel et al. "Characterization of Biomembranes by Spectral Ellipsometry, Surface Plasmon Resonance and Interferometry with Regard to Biosensor Application", Biosensors & Bioelectronics 9, pp. 139-146, 1994 Elsevier Science Publishers Ltd.

T.A. Ruzgas et al. "Ellipsometric Immunosensors for the Determination of γ-Interferon and Human Serum Albumin", Biosensors & Bioelectronics 7, pp. 305-308, 1992 Elsevier Science Publishers Ltd.

Haken Nygren et al. "Determination by Ellipsometry of the Affinity of Monoclonal Antibodies", Journal of Immunological Methods, 92, pp. 219-225, 1986 Elsevier Science Publishers Ltd.

John F. Place et al. "Opto-electronic Immunosensors: A Review of Optical Immunoassay At Continuous Surfaces", Biosensors 1, pp. 321-353, 1985 Elsevier Applied Science Publishers Ltd., England.

A. Brecht et al. "Biosensors: Fundamentals, Technologies and Applications" GBF Monographs, vol. 17, pp. 174-178, 1991 Germany.

Hakan Nygren et al. "Kinetics of Antibody-Binding to Surface-Immobilized Antigen: Influence of Mass Transport on the Enzyme-Linked Immunosorbent Assay (ELISA)", Journal of Colloid and Interface Science, vol. 107, No. 2 pp. 560-566, Oct. 1985 Academic Press, Inc.

Martin Malmsten et al. "Effects of Hydrophilization and Immobilization on the Interfacial Behavior of Immunoglobulins", Journal of Colloid and Interface Sicence 177, pp. 70-78, 1996 Academic Press, Inc.

Pentti Tengvall et al. "Temporal Studies on the Deposition of Complement on Human Colostrum IgA and Serum Immobilized on Methylated Silicon", Journal of Biomedical Materials Research, vol. 35, pp. 81-91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163-181, 1995 Humana Press Inc.

G. Elender et al. "Wetting and Dewetting of Si/SiO2-Wafers by Free and Lipid-Monolayer Covered Aqueous Solutions Under Controlled Humidity", Journal de Physique, II France 4 pp. 455-479, Mar. 1994.

C.F. Mandenius et al. "Coupling of Biomolecules to Silicon Surfaces for use in ellipsometry and other related techniques", Methods in Enzymology, vol. 137, pp. 389-394, 1988 Academic Press, Inc.

A.W. Flounders et al. "Patterning of immobilized antibody layers via photolithography and oxygen plasma exposure", Biosensors and Bioelectronics, vol. 12, No. 6 pp. 447-456, 1997 Elsevier Science Ltd., Great Britain.

A. Ahluwalia et al. "A comparative study of protein immobilization techniques for optical immunosensors", Biosensors and Bioelectronics 7, (1991) pp. 207-214, 1992 Elsevier Science Publishers Ltd.

Dr. Rudolf Oldenbourg "Metamorph Imaging System", http://www.image1.com/products/metapolscope/ Universal Imaging Corporation Last Updated Jun. 10, 1999 pp. 1-2.

Dr. Rudolf Oldenbourg "A new view on polarization microscopy", Nature, vol. 381, pp. 811-812, Jun. 27, 1996.

Clifford C. Hoyt et al. "Structural analysis with quantitative birefringence imaging", American Laboratory, pp. 34-42, Jul. 1999.

Dirk Honig et al. "Direct visualization of monolayers at the air-water interface by Brewster angle microscopy", J. Phys. Chem., pp. 4590 & 4592, 1991 American Chemical Society.

S. Henon et al. "Microscope at the Brewster angle: direct observation of first-order phase transitions in monolayers", Rev. Sci. Instrum. 62, (4) pp. 936-939, Apr. 1991 American Institute of Physics.

Gang Jin et al. "A biosensor concept based on imaging ellipsometry for visualization of biomolecular interactions", Analytical Biochemistry 232, pp. 69-72, 1995.

Pentti Tengvall et al. "Complement activation by 3-mercapto-1,2-propanediol immobilized on gold surfaces", Biomaterials vol. 17, No. 10 pp. 1001-1007, 1995 Elseviar Science Ltd., Great Britain.

H. Arwin "Spectroscopic ellipsometry and biology: recent developments and challenges", Thin Solid Films 313-314, pp. 7640774, 1998 Elsevier Science S.A.

Christopher Palmer "Diffraction Grating Handbook", pp. 35-44, 2000 Richardson Grating Laboratory, Rochester, New York.

Erwin G. Loewen "Diffraction Gratings, Ruled and Holographic", Applied Optics and Optical Engineering, vol. IX, pp. 33-71, Bausch and Lomb, Inc., Rochester, New York 1983 Academic Press, Inc.

* cited by examiner

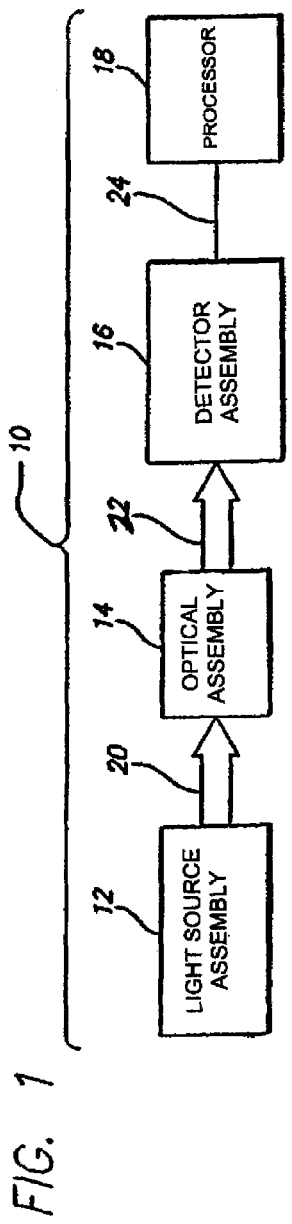
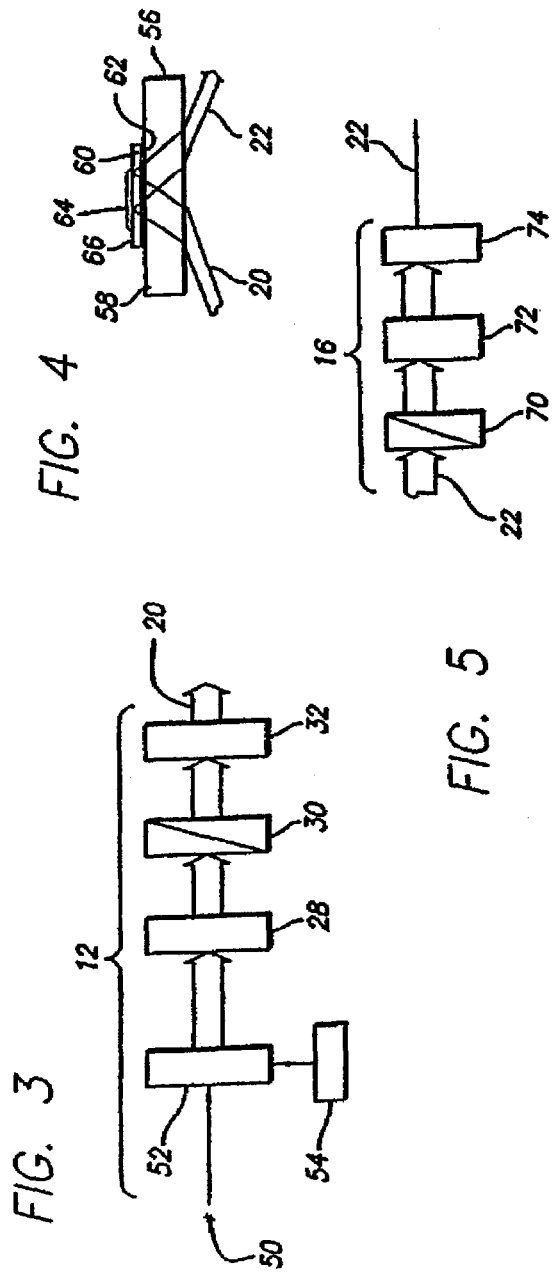

IMAGING METHOD AND APPARATUS

RELATED APPLICATIONS

This application is a continuation-in-part of U.S. patent application Ser. No. 10/602,555 filed on Jun. 23, 2003 now U.S. Pat. No. 6,859,280.

This application is also a continuation-in-part of U.S. patent application Ser. No. 10/046,620 filed on Jan. 12, 2002 now U.S. Pat. No. 6,833,920, which in turn is a continuation-in-part of U.S. patent application Ser. No. 09/614,503 filed on Jul. 11, 2000, now U.S. Pat. No. 6,594,011.

This application is also a continuation-in-part of U.S. patent application Ser. No. 09/838,700 filed on Apr. 19, 2001 now U.S. Pat. No. 7,023,547, which in turn is a continuation-in-part of U.S. patent application Ser. No. 09/614,503 filed on Jul. 11, 2000, now U.S. Pat. No. 6,594,011.

The above-mentioned U.S. patent application Ser. Nos. 10/602,555, 10/046,620, and 09/838,700, and U.S. Pat. No. 6,594,011 are incorporated by reference herein for all purposes.

BACKGROUND OF THE INVENTION

1. Field of Invention

This invention relates to imaging techniques and apparatus in conjunction with internal reflection at the boundary of an optically transparent material and more particularly to the use of such techniques and apparatus for detecting the presence, composition, quantity, and/or spatial distribution of substances on optically transparent substrates.

2. Discussion of the Related Art

This invention relates to imaging of a biochip (also referred to as a gene chip, protein chip, microarray and others). The formation of an array of biologically or chemically active spots on the surface of a substrate for identifying constituents in test material brought into contact with the array is well known. Typically, such processes require spots of, for example, oligonucleotides, cloned DNA, antibodies, peptides, receptors, enzymes, inhibitors, etc. which are processed to exhibit fluorescence, electroluminescence, current change, voltage change, etc. for providing a detectable signature for the presence of constituents in the material being tested.

SUMMARY

In accordance with the principles of this invention, light from a light source member providing a polarized light beam is directed through a transparent substrate and undergoes reflection, for example total internal reflection (TIR), at the surface of the substrate. Total internal reflection is described in: M. Born, and E. Wolf, "Principles of Optics", 6th ed., pp 47–51, Pergamon Press, Oxford, 1991. The reflected light is detected by a polarization-sensitive, two-dimensional array detector or other type of detector. The changes of the local polarization state in the beam's cross-section caused by a specimen array are employed to obtain information about the presence and composition of substances on the substrate surface for each point of the surface.

The total internal reflection at any point within the cross-section of the light beam causes a phase shift between the light component polarized in the plane of incidence and the component polarized perpendicular to the plane of incidence. The reflected light is detected by a polarization-sensitive detector such as a two dimensional array detector and the signal from this detector is then processed in a computer to provide two-dimensional information about substances on the surface of the specimen. Spatially distributed changes in polarization state in the cross-section of the reflected beam are indicative of the substances in the specimen in the location in the specimen array corresponding to a position in the detector.

In accordance with one embodiment of the present invention, an imaging apparatus is provided, including a light source emitting a polarized light beam, and an optical assembly including a control layer and a light reflection surface. The light beam is passed through the control layer and reflected by the light reflection surface to provide an evanescent field with controlled height and intensity adjacent the light reflection surface, the light reflection surface being adapted to provide thereon a specimen array such that the specimen array in the evanescent field causes spatially distributed polarization changes in the cross-section of the light beam. The apparatus further includes a detector positioned to detect the spatially distributed polarization changes in the light beam to provide an image of the specimen array.

In accordance with another embodiment of the present invention, an imaging apparatus is provided, including an optical assembly having a light reflection surface, wherein the light beam is reflected by the light reflection surface to provide an evanescent field adjacent the light reflection surface, the light reflection surface including coupling means for providing thereon a specimen array such that the specimen array in the evanescent field causes spatially distributed polarization changes in the cross-section of the light beam.

In accordance with yet another embodiment of the present invention, an imaging method is provided, including passing a polarized light beam into an optical assembly having a control layer and a light reflection surface, and providing an evanescent field with controlled height and intensity adjacent the light reflection surface using the control layer. The method further includes providing a specimen array in the evanescent field causing spatially distributed polarization changes in the cross-section of the light beam, and passing the reflected light beam out of the optical assembly where the spatially distributed polarization changes in the light beam are detected and processed to provide an image of the specimen array.

In accordance with yet another embodiment of the present invention, an imaging method is provided, including passing a polarized light beam into an optical assembly having a light reflection surface, which has coupling means for providing thereon an array of capture agents, and providing an evanescent field adjacent the light reflection surface. The method further includes providing molecules of interest such that the array of capture agents coupled with molecules of interest in the evanescent field cause spatially distributed polarization changes in the cross-section of the light beam, and passing the reflected light beam out of the optical assembly where the spatially distributed polarization changes in the light beam are detected and processed to provide an image of the array of capture agents coupled with the molecules of interest.

In accordance with yet another embodiment of the present invention, a cassette for use with an imaging apparatus is provided, the cassette including a light reflection surface including coupling means to allow formation thereon of a specimen array, a control layer configured to direct a polarized light beam from a light source to the light reflection surface, such that a reflection of the polarized light beam at the light reflection surface generates a controlled evanescent field in the vicinity of the specimen array, and a flow cell coupled to the light reflection surface, the flow cell including an inlet port and an outlet port for flowing analyte across the specimen array.

The apparatus and method of the present invention are especially adapted for imaging material in an aqueous solution. It is furthermore particularly suited for detecting attachment and detachment of analytes to a two-dimensional biomolecular array positioned on a light reflection surface as part of a molecular thin film system. In various applications a plurality of discrete specimen spots are presented in an array, where the method and apparatus will image the array so as to distinguish each of the discrete specimen spots. Advantageously, fluorescence or molecular tagging is not necessary but optional for use in this invention.

These and other features and advantages of the present invention will be more readily apparent from the detailed description of the embodiments set forth below taken in conjunction with the accompanying drawings.

BRIEF DESCRIPTION OF DRAWINGS

FIG. 1 is a block diagram of an illustrative system in accordance with the principles of this invention;

FIGS. 3, 4, and 5 are block diagrams of alternative portions of the system of FIG. 1.

Use of the same reference symbols in different figures indicates similar or identical items. It is further noted that the drawings may not be drawn to scale.

DETAILED DESCRIPTION

Figure 2:
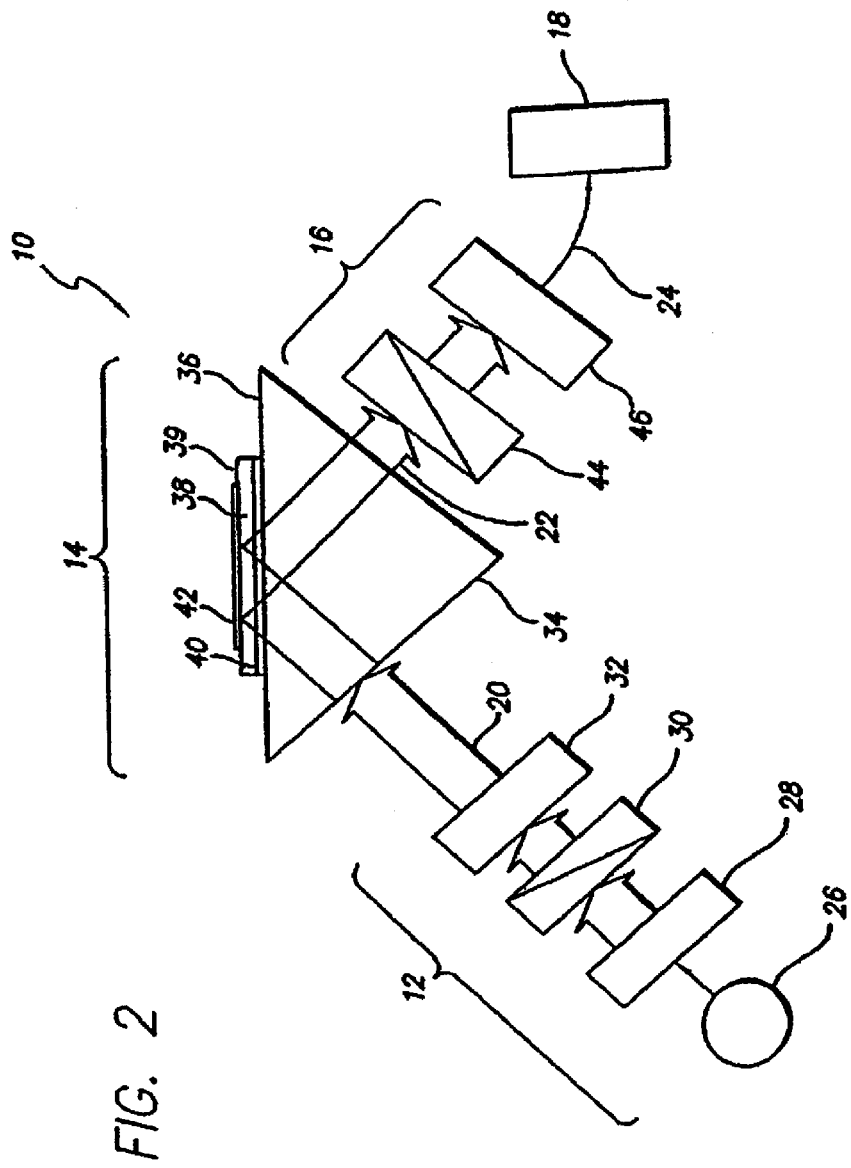
FIG. 2 is a block diagram of an embodiment of the system of FIG. 1.

The invention comprises a method and apparatus for analyzing a two-dimensional arrangement of chemical substances with an imaging technique. A polarized light beam of known polarization state is directed into an optical assembly, for example a total internal reflection member (TIR member), configured for reflection at a light reflection surface, for example a total internal reflection surface (TIR surface), and then exits the optical assembly. In the context of this document, superposition of reflections as encountered at a layered optical structure where the layer thicknesses are smaller than the coherence length of the illuminating light is referred to as a single reflection.

The chemical specimen is in place on or above the light reflection surface in the evanescent field of the reflected light beam. After reflection, the beam is passed to a polarization-sensitive two-dimensional detector such as a polarizer and a camera or other types of detectors. The reflected beam's content can then be processed to determine the change in polarization state, locally in the two-dimensional cross-section of the beam. This provides a spatially distributed map of change of polarization state in the specimen. A variety of techniques are available to determine the change in polarization such as measuring the deviation from a null condition or by comparing the input polarization state to the output polarization state.

The refractive index composition of the materials within the evanescent field determines the change in the polarization state of the beam due to the reflection at the light reflection surface. A two-dimensional variation of this composition within the light reflection surface is associated with a respective variation of the polarization state spatially distributed across the cross-section of the reflected light beam.

In one application, the chemical specimen forms a two-dimensional array of molecules (referred to herein as receptors and generally referred to as capture agents or affinity agents) with specific affinities towards respective other molecules (referred to herein as ligands). In this application, the invention is utilized to indicate the presence or absence or rate of binding between molecules and capture agents on the array. Such arrays commonly consist of a plurality of discrete specimen spots. The present method and apparatus images the array so as to distinguish each of the discrete specimen spots represented by the local change in polarization state in the cross-section of the reflected beam.

Subject to limitations in resolving power of the detector, the invention permits measurement of thickness and/or refractive index composition of the specimen under investigation with a very high resolution, in the sub angstrom range, spatially resolved over an entire area. It is noted that thickness and refractive index measurements are functions of the electronics of the detector and that spatial resolution is a function of the optics associated with the optical assembly. The invention is particularly useful in applications where the specimen is in an aqueous solution. In a particular application, the present invention is used to determine the presence of biological agents in a solution such as in immunosensor applications by measuring their attachment to antibodies on the TIR surface in the evanescent field. In another application, the present invention is used to determine the presence and structure of nucleic acid sequences in a solution by measuring their attachment to other nucleic acid sequences on the light reflection surface in the evanescent field. Described in more detail below are different embodiments of the invention.

FIGS. 1 and 2 show an apparatus which implements one embodiment of the invention. As shown in FIG. 1, the apparatus 10 can be described conveniently as consisting of three general portions. A first portion includes a polarized light source assembly 12, a second portion includes an optical assembly 14 providing a control layer and/or a light reflection surface, and a third portion includes a polarization-sensitive imaging detector assembly 16 which can employ for example a two-dimensional array detector.

Data from detector assembly 16 is sent by an electrical signal along a connector 24 to processor 18 such as a specially programmed computer and user access system including an image display. Data can be presented as an image, a data table, a graph, or in other forms. The polarized light source assembly 12 passes polarized light of known polarization state 20, which may be varied or varying to optical assembly 14 where a light beam reflection occurs. Reflected light 22, having a changed polarization state, passes to detector assembly 16, where it is recorded spatially over the cross-section of the beam. The recorded data is sent to processor 18 where the change of polarization state is determined to provide a spatially resolved map of changes in polarization state. Where the specimens are presented as an array of discrete spots, each spot will be imaged for its change in polarization state within the spot area.

FIG. 2 shows a more detailed schematic block diagram of a preferred embodiment. The polarized light source assembly 12 has a light source 26, a beam forming member 28 (if the nature of the light source is such as to make beam forming useful or necessary), a polarizer 30, and an optical retarder 32.

The optical assembly 14 has an optical element 34 which has an optical surface 36. Also shown is a control layer 38 over optical surface 36, and between them an index matching substance 40. A specimen 42 is positioned on light reflection surface 39 of control layer 38 in one example.

In one embodiment of the invention, optical element 34 is a prism configured along with control layer 38 in relationship to the incoming light beam 20 and the exiting light beam 22 such that the beam reflects only a single time at light reflection surface 39 and then exits the prism. If the specimen is placed directly on the optical surface 36, then the optical surface 36 would be the light reflection surface. But this is not the usual application, since the specimen (such as a biochip) is usually prepared more conveniently on a specimen slide and placed in the apparatus. In one example, control layer 38 with light reflection surface 39 can act as a specimen slide or control layer 38 can operate in conjunction with a specimen slide. However constructed, the invention incorporates an optical structure having a light reflection surface and the beam reflects at the reflection surface between entering and leaving the optical structure. In other words, there is a light reflection surface in optical contact with the specimen, such that the evanescent field associated with the total internal reflection interacts with the specimen.

In one embodiment, the post-reflection detector assembly 16 has a polarizer 44 and an imaging detector, for example a two-dimensional array detector 46 and preferably a camera of the CCD or CMOS array type. The processor 18 is a specially programmed computer (or processor) and output means for processing the imagery into a representation of film thickness variations spatially resolved over the cross-section of the area imaged. The imaging is acquired by detecting changes spatially distributed in the local polarization state in the beam's cross-section caused by the total internal reflection. This provides information about the presence and composition in the array of substances on the substrate surface for each resolvable point on the surface. Different polarization state changes are included in the cross-section of the reflected beam indicative of the substances on the specimen in the location in the specimen array corresponding to a position in the detector.

Processor 18 receives the data as an electrical signal (on connector 24) and characterizes the change of polarization state spatially over the two-dimensional array. In processor 18, the analysis and processing is done in one embodiment by comparing the known polarization state of the incoming light from the light processing assembly 12 with the changed polarization state of the reflected light 22, spatially resolved two-dimensionally within the beam which provides a map of spatially distributed points or spots in the specimen array. The polarization shift is then analyzed by processor 18 to provide information of the presence and properties of elements in the chemical specimen. Other known techniques, such as null processing can be used to determine the change in polarization state.

Alternatively, light source 26 may be an LED, an SLD (Super Luminescent Diode), an incandescent light source, or a laser. If an LED or SLD is used, the set-up shown in FIG. 2 is appropriate, where the beam-forming member 28 is a collimator. If an incandescent light source is used, an optical filter is also used. In one embodiment, light source 26 for the apparatus is a quasi-monochromatic light source of moderate bandwidth. In accordance with the invention light source 26 is preferably an LED of moderate bandwidth. Preferably the bandwidth is a full width half maximum wavelength in the range of about 10 nm–50 nm, and more preferably a full width half maximum wavelength in the range of about 30 nm–50 nm.

In an alternative embodiment, optical retarder 32 can be placed instead to receive the exiting light beam 22 at a location before polarizer 44.

FIG. 3 shows an additional embodiment. In embodiments in which the light source is a laser 50, a moving diffuser 52 is adapted to produce speckle-offsetting fluctuation of the minima and maxima in the speckle pattern caused by the laser. The moving diffuser 52 is attached to a mechanical actuator 54 which is preferably a motor and servo-apparatus for providing the speckle offsetting fluctuations. The light beam then proceeds through the beam-forming element 28, the polarizer 30, and the optical retarder 32, exiting light source assembly 12 as light beam 20.

Polarizer 30, in embodiments as shown in FIGS. 2 and 3, employs a polarizer of selected known polarization state. Polarizer 30 may be of the type having a mechanical actuator driven by a motor control signal so as to enable the variation and selection of the polarization state of the light beam 20.

As mentioned above, the optical element 34 (of FIG. 2) either alone or in combination with an index-matched substance may be arranged for use with a specimen in various ways to define an optical assembly so long as the specimen is in the evanescent field of the reflected beam.

As noted above, the specimen 42 (of FIG. 2) could be set directly on the optical surface 36 in which case the optical surface 36 would be the light reflection surface. But this is inconvenient and repeated use is likely to degrade the optical quality of the optical surface 36. Therefore, consistent with common practice in which a biochip or other chemical assay specimen is provided, a specimen slide or other supporting apparatus is employed. It is common in a biochip to provide an array of discrete specimen spots supported on a structure for obtaining analysis of each spot. The term total internal reflection optical element refers to known optical elements alone or in combination with other elements which provide the phenomenon known as total internal reflection. FIG. 2 shows use of a prism combined with a control layer 38 having a light reflection surface 39.

FIG. 4 shows an alternative optical arrangement in which a control layer 60 is placed above an index matching substance 62, which in turn is placed above a flat optical member 56 having an upper surface 58. A specimen 64 is mounted above a light reflection surface 66, which in one example is the top of control layer 60. The beam 20 enters the optical assembly, is refracted as it enters, and leaves optical member 56 after a single reflection at light reflection surface 66. Other mechanisms for providing total internal reflection and an evanescent field can be employed in practicing this invention as long as the specimen is placed so as to be in the evanescent field associated with the reflection.

As seen in FIG. 5, the post-reflection detector assembly 16 through which the beam 22 passes can alternatively consist of a polarizer member 70, a beam forming member 72, and an imaging detector 74 such as a two dimensional array detector or other type of imaging detector.

As provided in the embodiments above, optical assembly 14 includes a control layer 38 having a light reflection surface 39 (FIG. 2) and alternatively, an optical assembly includes a control layer 60 having a light reflection surface 66 (FIG. 4).

Control layers 38 and 60 each provide an optical element to their respective light reflection assemblies such that parameters of the evanescent wave, for example height (which is related to penetration of the wave into the medium) and intensity (which is related to how fast the wave decays in the medium), may be shaped and further controlled for optimizing the image of the specimen array. Depending upon control layer parameters such as thickness and optical property (including refractive index and reflectivity characteristics), control layers 38 and 60 advantageously allow for control over generation of evanescent waves at less acute angles and/or at specific areas of the specimen slide for flexible control over background noise. By controlling the depth of penetration of the evanescent wave, noise from the carrier medium may be reduced. For example, if the depth of penetration of the evanescent wave is no deeper than the net height of the receptor/ligand complex for which the biochip is designed, contribution of noise and drift from the media will be minimal.

In one example, the control layer may be comprised of glass, liquid crystal, a metal film, and/or semiconductor material. In a further example, the liquid crystal may be charged to shutter, modulate, and/or optimize optical properties of the control layer thereby allowing for control over the evanescent wave that is generated adjacent the control layer. The metal film may include gold, silver, titanium, and/or chromium. In yet another example, potential may be applied to the metal film to change electrical conductance of the metal film in order to control the height and intensity of the evanescent wave.

The control layer is key to the critical angle. Higher refractive index materials allow for generation of TIR and evanescent waves (and therefore imaging) at less oblique angles, thereby improving the image quality by reducing aspect ratio distortion and focal plane tilting. Use of a substrate material that provides a refractive index contrast between the analyte and the fluid medium is advantageous. The greater the spread, the greater the sensitivity.

Control layers 38 and 60 may also each provide a light reflection surface that interfaces with specimens 42 and 64, respectively, and allow for exact placement of receptors for binding of molecules of interest. Coupling means having affinities for molecules of interest, such as biomolecular substances, may be included on the light reflection surface. Accordingly, the coupling means is used to couple a receptor/capture agent to the light reflection surface such that information about molecules of interest may be gathered. Advantageously, control layers 38 and 60 allow for flexible control over receptor specific regions utilizing for example particular proteins.

Control layers 38 and 60 may include in one example, a light reflection surface comprised of material selected from semiconductors, metals (such as gold, silver, titanium, or chromium), and/or plastics. In a further example, the light reflection surface may be comprised of a silane material, for example glass, and the coupling means may include a silanizing agent with affinity for biomolecules, such as an epoxy or aldehyde, to silanize the light reflection surface. In yet a further example, the light reflection surface may be comprised of metal, for example gold, silver, titanium, and/or chromium, and the coupling means may include a sulfur-containing compound, such as a thiol, to attach the capture agent or derivatize the light reflection surface for additional layers. Advantageously, thiols are present or easily coupled to a variety of receptors/capture agents such as proteins, nucleic acids, and polyethylene glycols by a variety of attachment chemistries.

Immobilization of receptors directly on glass surfaces may be by means of various members of the classes of aminosilanes, aldehyde silanes, and epoxy silanes covalently bonded to the glass surface by means of Schiff base, Schiff base, and epoxide formation, respectively, and to the receptor or a chemically derivatized portion thereof. Synthetic oligonucleotides may also be directly coupled to glass by means of phosphoramidite chemistry rather than by attaching a reactive moiety.

Similarly, linear or branched carbohydrates, lipids or other synthetic polymers bearing the aforementioned amines, aldehydes, or epoxy moieties may be used for increasing surface area for receptor immobilization, for tailoring surface energy (wetting), and for preventing non-specific adsorption by ligand molecules. A lipid bilayer may serve as an immobilization layer for study of receptor molecules that typically reside at such a layer in living organisms. Surface-bound avidin or biotin can serve as an intermediate linker to avidinylated or biotinylated receptor molecules or yet other intermediary layers.

Nitrocellulose has a convoluted and porous surface with a large surface area and is a traditional charge-based nucleic acid and protein binding medium traditionally used for separation and for "blotting" experiments. Thinner nitrocellulose than is traditionally employed in these techniques is particularly advantageous for use within the present invention. Porous nitrocellulose membranes are typically a micron thick or more, but nitrocellulose can be cast into solid objects, such as films or slides. Cast nitrocellulose has a refractive index of about 1.62 with a smooth reflective surface and can be used as a specimen slide substrate or prism/grating substrate as well as a biomolecular attachment point. However, because the cast material has a small surface area and the binding of material will be sparse, a surface roughened by less than $\lambda/2$ by means of solvent etching, adsorption, growth, or mechanical means is advantageous. The chemical derivatization and surface charge manipulation of nitrocellulose may also be advantageous. A wide variety of other engineering plastics used in manufacturing multi-well (micro-titer) plates can also be derivatized to covalently bind or electrostatically hold receptor molecules. Engineering plastics that are transparent and have higher refractive indices than 1.6 are advantageous for increased sensitivity and image quality.

The method and apparatus of the present invention can be used in combination with biochips of the type having discrete specimen spots or a micro-titer plate containing an array of discrete spots or locations for analysis, where the detected change in polarization state is spatially related to the discrete locations in the reflected beam. Therefore, as used herein the control layer and specimen refers to any type of chemical or biological array that is desired to be examined. The foregoing described apparatus and methods are especially beneficial for imaging materials in an aqueous medium.

The invention as described above provides an extremely sensitive optical imaging system for real-time imaging of the binding status of biochip array elements on the surface of an optically transparent material such as a glass or plastic chip. An exemplary monitored array of a 15 mm square inscribed in a 20 mm circular field, with discrete specimen spots of size commensurate with the lateral resolution of the imaging optics, results in fully parallel, continuous real-time readout of up to 5 million sensor fields. Sensor sensitivity to surface attachment is in the femtogram/mm.sup.2 range (e.g., one DNA per square micron).

The apparatus of FIG. 1 operates by imaging the pattern of reactions on the biochip. Those reactions produce changes in the height, surface concentration, and/or refractive index of the material that reacts at each spot. The area imaged could be the entire biochip array or a portion of the entire biochip array. By providing an array of spots of different materials, different constituents in test material flowed over the spots bind in a manner which identifies those constituents. By including in a computer memory the positions of the various materials in the different spots of the array, the image produced by the apparatus of FIG. 1 identifies the constituents in the test material and can also determine the rate at which the reactions occur by imaging successively over time. With the apparatus described, height differences can be imaged dynamically over such short periods of time that intermediate height change readings can be recorded and therefore height change rates can be determined as well as allowing comparison of the rate of height change or intermediate amount of height change among the spots on the biochip array.

A process using the apparatus and a biochip is as follows:

Place the biochip surface in a flow cell in combination with the apparatus such that the surface of the slide which has the spots is the light reflection surface, in one example a TIR surface; initially calibrate the apparatus, such that light reflected from the biochip yields a fully-linear polarization; and adjust the analyzer to a null position to fully block the linearly polarized light.

When the null position is achieved, every region where the chip (slide) surface deviates from the initial state stands out as a bright spot the intensity of which is directly related to the thickness (height) differences induced by the deviation. A solution containing target molecules are flowed over the biochip surface. The intensity changes caused by changes in the polarization of the light reflected by the biochip may be monitored continuously across the array to study thickness changes that occur on the biochip. The relative intensity measured at the detector is related to the sample parameters and the setting of the polarizing elements using computer programs based on a detailed "Jones calculus" or "Mueller calculus" sensor system description. With these programs, theoretical plots are fitted to the acquired measurement data sets, and the outputs' dependence on parameter variations can be visualized.

At the start of the procedure, the apparatus is adjusted so that the image of the entire biochip is homogeneously dark. As the target molecules begin to bind to the reference probes the intensity of the images of the spots increases. The intensity is expected to be the highest for high affinity interactions and mild changes are expected for low affinity interactions. The rate of intensity change can be related to the constraints of the system on affinity. For example, using a properly prepared biochip, in a single procedure, the affinity measurements for multiple receptors can be performed. Moreover, the effect of binding density (because different concentrations of receptors are used in spotting) can also be measured to determine if steric constraints (e.g., geometric interference, crowding, etc.) exist and to demonstrate the dynamic range of the measurements.

Reference is made to nulling ellipsometry but off-null or phase-modulation ellipsometry are also within the scope of the present invention. Advantageously, both off-null and phase-modulation ellipsometry can utilize improved noise characteristics of two-dimensional detectors (e.g., CCD, CMSOS) at higher levels of light throughput.

Although reference is made to biochips in the example above, the procedure and the results apply generally to chemically sensitive materials on a light reflection surface.

The invention has been described above in terms of a prism having a light reflection surface, and having on the surface an array of molecular spots. In another embodiment, also described above, the array is formed on a separate slide or control layer positioned on the prism with index matching fluid between them so that only the upper surface of the slide or control layer forms the light reflection surface.

The above-described embodiments of the present invention are merely meant to be illustrative and not limiting. Various changes and modifications may be made without departing from this invention in its broader aspects. Accordingly, the invention is not limited to particular structures, dimensions, or process parameters. Therefore, the appended claims encompass all such changes and modifications as falling within the true spirit and scope of this invention.

We claim:

1. An apparatus for imaging, comprising:
    a light source emitting a polarized light beam;
    an optical assembly including a control layer and a light reflection surface, wherein the light beam is passed through the control layer and reflected by the light reflection surface to provide an evanescent field with controlled height and intensity adjacent the light reflection surface, the light reflection surface being adapted to provide thereon a specimen array such that the specimen array in the evanescent field causes spatially distributed polarization changes in the cross-section of the light beam; and
    a detector positioned to detect the spatially distributed polarization changes in the light beam to provide an image of the specimen array.

2. The apparatus as in claim 1, wherein the control layer comprises glass, liquid crystal, and/or semiconductor material.

3. The apparatus as in claim 1, wherein the control layer has a thickness for controlling evanescent field generation.

4. The apparatus as in claim 1, wherein the control layer has a refractive index for controlling evanescent field generation.

5. The apparatus as in claim 1, wherein the control layer has a reflectivity characteristic for controlling evanescent field generation.

6. The apparatus as in claim 1, wherein the light reflection surface includes a metal film to which potential is applied.

7. The apparatus as in claim 6, wherein the metal film is comprised of gold, silver, titanium, and/or chromium.

8. The apparatus as in claim 1, wherein the specimen array includes a two-dimensional array formed of multiple fields comprising biomolecular substances.

9. The apparatus as in claim 8, wherein the biomolecular substances are proteins, peptides, carbohydrates, lipids, and/or polynucleotide sequences.

10. An apparatus for imaging, comprising:
    a light source emitting a polarized light beam;
    an optical assembly including a light reflection surface, wherein the light beam is reflected byte light reflection surface to provide an evanescent field adjacent the light reflection surface, the light reflection surface including coupling means for providing thereon a specimen array such that the specimen array in the evanescent field causes spatially distributed polarization changes in the cross-section of the light beam; and
    a detector positioned to detect the spatially distributed polarization changes in the light beam to provide an image of the specimen array.

11. The apparatus as in claim 10, wherein the light reflection surface is comprised of material selected from the group consisting of semiconductors, metals, and plastics.

12. The apparatus as in claim 10, wherein the light reflection surface is comprised of silane and the coupling means includes a silanizing agent.

13. The apparatus as in claim 10, wherein the light reflection surface is comprised of metal and the coupling means includes a sulfur-containing compound.

14. The apparatus as in claim 13, wherein the metal includes gold, silver, titanium, and/or chromium.

15. The apparatus as in claim 13, wherein the sulfur-containing compound is a thiol.

16. The apparatus as in claim 10, wherein the light reflection surface is comprised of plastic.

17. The apparatus as in claim 10, wherein the coupling means has an affinity for biomolecular substances.

18. The apparatus as in claim 10, wherein the specimen array includes a two-dimensional array formed of multiple fields comprising biomolecular substances.

19. The apparatus as in claim 18, wherein the biomolecular substances are proteins, peptides, carbohydrates, lipids, and/or polynucleotide sequences.

20. A method of imaging, comprising:
    passing a polarized light beam into an optical assembly including a control layer and a light reflection surface;
    providing an evanescent field with controlled height and intensity adjacent the light reflection surface using the control layer;
    providing a specimen array in the evanescent field causing spatially distributed polarization changes in the cross-section of the light beam; and
    passing the reflected light beam out of the optical assembly where the spatially distributed polarization changes in the light beam are detected and processed to provide an image of the specimen array.

21. The method of claim 20, wherein an optical property of the control layer is used to control the height and intensity of the evanescent field.

22. The method of claim 21, wherein the optical property of the control layer is selected from the group consisting of thickness, refractive index, and reflectivity characteristic.

23. The method of claim 20, wherein the control layer is comprised of liquid crystal that is used to control optical properties of the control layer.

24. The method of claim 20, wherein the light reflection surface is comprised of a metal.

25. The method of claim 24, further comprising applying a potential to the metal to control the height and intensity of the evanescent field.

26. A method of imaging, comprising:
    passing a polarized light beam into an optical assembly including a light reflection surface having coupling means for providing thereon an array of capture agents;
    providing an evanescent field adjacent the light reflection surface;
    providing molecules of interest such that the array of capture agents coupled with molecules of interest in the evanescent field cause spatially distributed polarization changes in the cross-section of the light beam; and
    passing the reflected light beam out of the optical assembly where the spatially distributed polarization changes in the light beam are detected and processed to provide an image of the array of capture agents coupled with the molecules of interest.

27. The method of claim 26, wherein the coupling means is used to couple a capture agent to the light reflection surface.

28. The method of claim 26, wherein the light reflection surface is comprised of glass.

29. The method of claim 28, wherein the coupling means includes a silanizing agent to silanize the light reflection surface.

30. The method of claim 26, wherein the light reflection surface is comprised of metal.

31. The method of claim 30, wherein the coupling means includes a sulphur-containing compound to derivatize or couple capture agents to the light reflection surface.

* * * * *